(12) United States Patent
Hastings et al.

(10) Patent No.: US 6,224,871 B1
(45) Date of Patent: May 1, 2001

(54) DIETARY SUPPLEMENT FOR NUTRITIONALLY PROMOTING HEALTHY JOINT FUNCTION

(75) Inventors: Carl W. Hastings, Glencoe; David J. Barnes, Wildwood, both of MO (US); Christine A. Daley, Columbia, IL (US)

(73) Assignee: Reliv International, Inc., Chesterfield, MO (US)

( * ) Notice: Subject to any disclaimer, the term of this patent is extended or adjusted under 35 U.S.C. 154(b) by 0 days.

(21) Appl. No.: 09/038,394

(22) Filed: Mar. 11, 1998

(51) Int. Cl.[7] .................... A61K 35/78; A61K 38/01; A61K 38/02; A61K 47/46
(52) U.S. Cl. .................... 424/195.1; 424/196.1; 424/825; 424/886; 424/439; 514/2; 514/21
(58) Field of Search ..................... 424/439, 440, 424/441, 195.1, 196.1, 825, 886; 514/886, 2

(56) References Cited

U.S. PATENT DOCUMENTS

| | | | |
|---|---|---|---|
| 4,804,745 | 2/1989 | Koepff | 530/356 |
| 5,376,379 | * 12/1994 | Fabre | 424/450 |
| 5,494,668 | * 2/1996 | Parwaedhan | 424/195.1 |
| 5,536,506 | * 7/1996 | Majeed | 424/464 |
| 5,888,514 | * 3/1999 | Weisman | 424/195.1 |

* cited by examiner

Primary Examiner—F. J. Moezie
(74) Attorney, Agent, or Firm—Tilton Fallon Lungmus

(57) ABSTRACT

A dietary supplement for nutritionally promoting healthy joint function in human subjects is disclosed. The supplement includes as a major ingredient a protein derived from the enzymatic hydrolysis of collagen in combination with lesser proportions of glucosamine sulfate, ginkgo biloba, borage oil powder, turmeric, *boswellia serrata*, ashwagandha, *piper nigrum* extract, and a herbal blend.

5 Claims, No Drawings

DIETARY SUPPLEMENT FOR NUTRITIONALLY PROMOTING HEALTHY JOINT FUNCTION

BACKGROUND AND SUMMARY OF THE INVENTION

Degenerative joint diseases, commonly known as orthroses, are most frequently found in bradytrophic tissue (tendon, cartilage) which is known to show little or no blood flow and, because of its slow metabolism, is incapable of responding to external noxious influences either with inflammatory and or with regenerative processes. As brought out in Koepff et al U.S. Pat. No. 4,804,745, clinical investigations have now led to the discovery that peptides soluble in cold water, and specifically those from a group of hydrolyzed collagens, are suitable for the treatment of orthoses. Particularly suitable is an enzymatically hydrolyzed collagen having an average molecular weight of from 10,000 to 80,000 daltons. Such enzymatically hydrolyzed collagen is almost flavorless or neutral in flavor, is soluble in cold water, and, unlike denatured collagen (gelatin) is incapable of binding significant amounts of water.

Collagen is a fiber protein forming the main constituent of the supporting tissue and connective tissue in animals (including humans) and, more particularly, is found in the skin, tendons and bones. Therefore, hydrolyzed collagen, and specifically enzymatically hydrolyzed collagen, may be produced from animal skin, animal bones, and other sufficiently purified connective tissue. Such enzymatically hydrolyzed collagens have previously been used in the pharmaceutical industry as tabletting aids, encasing agents and fillers. U.S. Pat. No. 4,804,745 describes that clinical investigations and double blind studies have now established that these enzymatically hydrolyzed collagens, taken in an amount of from 5 to 12 g per day, have alleviating effects on orthoses and also produce an analgesic effect which tends to reduce the need for administering other analgesics.

Recent studies have also shown the beneficial effects of glucosamine sulfate and its relationship with the symptoms of osteoarthritis, the most common form of arthritis. Glucosamine sulfate, which is naturally found in high concentrations in joint structures, is a stable, tasteless and water-soluble nutrient. It is readily absorbed from the intestines, stays in the blood for several hours, and very little is excreted. Glucosamine sulfate, taken as a dietary supplement, has been shown to exert a protective effect against joint destruction and is selectively used by joint tissues, exerting a dramatic positive effect in reducing arthritic symptoms and promoting healthy joint function. In particular, glucosamine stimulates the body's manufacture of collagen, the protein portion of the fibrous substance that holds joints together. Collagen is the main component of the shock-absorbing cushion called articular cartilage, and glucosamine is therefore a necessary nutrient in the production of cartilage and synovial fluid. However, the body's production of glucosamine decreases as a person ages, thereby inhibiting the new growth of cartilage destroyed through wear and tear.

The composition of this invention is a dietary supplement containing both glucosamine sulfate and protein derived from the enzymatic hydrolysis of collagen in combination with certain antioxidants, anti-inflammatory agents, thermo-nutrients for increasing absorption and utilization of other nutrients, and an herbal blend composed of ingredients that coact with other components to promote healthy joint function. More specifically, the dietary supplement takes the form of an essentially dry mixture of 78% to 90% protein derived from the enzymatic hydrolysis of collagen, 2% to 6% glucosamine sulfate, 2% to 5% ginkgo biloba (*Salsburia adiantifolia*), 0.8% to 1.5% borage oil powder (*Borago officinalis*), 0.3% to 0.7% turmeric (*Curcuma longa*), 0.01% to 0.03% *Boswellia serrata*, 0.5% to 0.7% ashwagandha (*Withania sominfera*), 0.04% to 0.08% *Piper nigrum* extract, and 5% to 10% herbal blend. In a preferred embodiment, the herbal blend includes cat's claw powder (*Uncaria tomentosa*), sarsaparilla root (*Smilax ornata*), licorice root (*Glycyrrhiza glabra*), kelp (*Ascophyllum nodosum*), burdock root powder (*Arctium lappa*), alfalfa powder (*Medicajo sativa*), barley grass (*B. Hordeum vulgare L.*), echinacea root (*Echinacea purpurea*), yucca extract (*Yucca schidigera*), bilberry extract (*Vaccinium myrtillus*), devil's claw powder *Harpagophytum procumens*, capsicum powder (*Capsicum annum linne* var. *Longum sendt capsuccum*) celery seed powder, and aloe vera extract.

Once the essentially dry mixture has been blended, the. composition can be delivered enterally as a beverage. The beverage is prepared by dissolving the proper amount of the essentially dry mixture in water, juice, milk or any other drinkable liquid. The recommended serving size is 7 to 10 g of the essentially dry mixture, optimally 8.5 g of that mixture, in a selected beverage. The recommended serving should be consumed once each day.

DETAILED DESCRIPTION OF PREFERRED EMBODIMENT

A major ingredient of the dietary supplement of this invention is hydrolyzed collagen, particularly enzymatically hydrolyzed collagen. Such material consists of a series of 19 amino acids joined in chains by peptide bonds. These are the same amino acids that comprise the framework of human cartilage, and are required for its generation. Enzymatically hydrolyzed collagen may be prepared by cutting, washing, and enzymatically hydrolyzing fresh or connective tissue in a tank fitted with a stir, followed by inactivation of the enzyme, separation, filtration, re-concentration, sterilization, and spray drying. The product is a whitish to yellow powder that is soluble in cold water, neutral in flavor, and of particle sizes less than about 0.5 mm. The average molecular weight falls generally within the range of about 10,000 to 80,000daltons. Higher molecular weight preparations are not sufficiently or as readily soluble in cold water, and lower molecular weight preparations are more difficult to bring into acceptable forms for application. Such enzymatically hydrolyzed collagen is commercially available under the designation "Arthred" from Traco Labs, Champaign, Ill. Further information concerning such enzymatically hydrolyzed collagen is set forth in Koepff et al U.S. Pat. No. 4,804,745, the disclosure of which is incorporated herein by reference. The patent discloses some of the double blind studies conducted with such enzymatically hydrolyzed collagen, the comparative clinical investigations revealing good compatability and intakeability with particularly good efficiency against orthroses being observed.

Glucosamine is an amino sugar normally found in humans and derived from glucose. It is considered the starting point for the synthesis of macro-molecules such as glycoproteins, glycolipids, and glyco-aminoglycans or mucopolysaccharides. Glycosamine sulfate is one of the biological chemicals involved in the formation of cushioning ingredients for joint fluids and surrounding tissues and contributes to make synovial fluid thick and elastic in joints and vertebrae.

Numerous studies have shown the beneficial effects of glucosamine sulfate and its relationship with the symptoms of osteoarthritis, the most common form of arthritis. Such double blind studies reveal that the oral administration of glucosamine sulfate is effective in reducing articular pain, joint tenderness and swelling, and the restrictions on active and passive movements, and tends to rebuild damaged cartilage, thereby restoring articular function in arthrosic patients.

The herbal components of the dietary supplement of this invention include ginkgo biloba and turmeric, both known for their properties as antioxidants and, in the case of turmeric, its anti-inflammatory properties. Turmeric is a rich source of curcuminoids, particularly curcumin, demethoxycurcumin, and bisdemethoxycurcumin. Continuing laboratory and clinical research indicate that turmeric and its phenolics have unique antioxidant and anti-inflammatory properties. Sharma, O. P., "Antioxidant Activity of Curcumin and Related Compounds," Biochem. Pharmacol. 25:1811 (1976); Scrimal, R. C., et al, "Pharmacology of Diferuloyl Methane (Curcumin), A Non-Steroidal Anti-Inflammatory Agent," J. Pharm. Pharmacol. 25:447 (1973). Such herbs are widely available in powder form, as is borage oil powder, also known as an anti-inflammatory agent as well as a supplier of fatty acids.

Other anti-inflammatory compounds in this dietary supplement are *boswellia serrata* and ashwagandha. *Boswellia serrata*, with boswellic acids as the active principle, are reported effective in various forms of arthritis, having been found to improve blood supply to the joints and prevent breakdown of tissues affected by arthritis. Clinical trials have revealed its effectiveness in reducing pain and morning stiffness as well as improving grip strength and physical performance. It is regarded as a non-steroidal anti-inflammatory compound without the side effects caused by non-steroidal analgesics such as aspirin.

Ashwagandha, also known as Indian ginseng, is a root extract described in the literature as an adaptogen or vitalizer and is used as a restorative or rejuvenative, particularly in the management of chronic diseases. It has anti-inflammatory and analgesic properties, it lowers blood pressure, protects the liver from toxins, and protects an organism from the results of physical stress. It has been found to increase the state of NSIR (non-specifically increased resistance) of the human body by offering protection against the deleterious effects of stress.

*Piper nigrum* extract has been known for its medicinal use dating back to the seventh century B.C. and experimental evidence shows it to be a thermonutrient capable of enhancing the bioavailability of other drugs and essential nutrients. As noted in Majeed et al U.S. Pat. No. 5,536,506, the disclosure of which is incorporated herein by reference, the metabolic pathways for a nutrient and a drug are different in that a nutrient sustains basic metabolism and physiological functions of an organism while a drug is utilized as an adjunct to basic metabolism to restore homeostasis to the physiological functions. In the context of this invention, *piper nigrum* extract is considered to increase the absorption of nutrients and to increase their metabolic utilization. Its inclusion in this nutritional supplement is intended to enhance the crossing-over of nutrients and botanical compounds through biological barriers such as, but not limited to, the gastrointestinal epithelium.

The nutrients and nutritional supplements included in the composition of the present invention are available commercially. The herbal compounds are generally available in powder form as a dried ethanol extract of a particular plant. For example, ginkgo biloba is from an ethanol extract of the ginkgo biloba plant and *boswellia serrata* is from an ethanol extract of *boswellia serrata* roots. Turmeric consists of curcuminoids from an ethanol extract of *cucuma longa* plant. *Piper nigrum* extract may be produced by the method of isolation of piperine disclosed in U.S. Pat. No. 5,536,506, and the compound obtained in such manner is commercially available as "Bioperine" from Sabinsa Corporation.

The dietary supplement is an essentially dry mixture of 78% to 90% protein derived from the enzymatic hydrolysis of collagen, 2% to 6% glucosamine sulfate, 2% to 5% ginkgo biloba, 0.8% to 1.5% borage oil powder, 0.3% to 0.7% turmeric, 0.01% to 0.03% *boswellia serrata*, 0.5% to 0.7% ashwagandha, 0.04% to 0.08% *piper nigrum* extract, and 5% to 10% herbal blend. Optionally included in the supplement are up to 3% natural and artificial flavoring agents and up to 5% lecithin, the latter being included to facilitate processing of the blend during manufacture.

The herbal blend, which constitutes 5% to 10%, may itself contain up to 20% (preferably 8% to 15%) of each of the following ingredients: cat's claw powder, also known as processed cat's claw bark (*Uncaria tormentosa*), sarsaparilla root, licorice root, kelp, burdock root powder, alfalfa powder, barley grass, and echinocea root. Additionally, the herbal blend may also include up to 7% of each of the following: yucca extract, bilberry extract, devil's claw powder, also known as processed cat's claw bark (*Uncaria tormentosa*), capsicum powder, celery seed powder, and aloe vera extract.

While the ingredients identified above are known and commercially available, the following sources are identified for further reference: glucosamine sulfate, Seltzer Chemicals, Carlsbad, Calif.; ginkgo biloba and kelp, Chart Corp., Patterson, N.J.; borage oil powder, Traco Labs, Champaign, Ill.; turmeric, *boswellia serrata*, and Bioperine, Sabinsa Corp., Piscataway, N.J.; cat's claw powder, sarsaparilla root, yucca extract, bilberry extract, and celery seed powder, Stryka Botanicals, Somerville, N.J.; ashwagandha, Fabrichem, Fairfield, Conn.; licorice root, burdock root powder, alfalfa powder, echinocea root, devil's claw powder, and capsicum powder, Botanicals International, Long Beach, Calif.; barley grass, Vitarich Foods Inc., Naples, Fla.; aloe vera extract, Aloe Corp., Broomfield, Colo.

The following examples are not intended to be limiting in any way, but demonstrate some of the preferred embodiments of the present invention.

EXAMPLE 1

A herbal blend suitable for use in the dietary supplement of this invention contains the following herbs in the percentages indicated: cat's claw powder 10.75%, sarsaparilla root 10.75%, licorice root 10.75%, kelp 10.75%, burdock root powder 10.75%, alfalfa powder 10.75%, barley grass 10.75%, echinacea root 10.75%, yucca extract 5.38%, capsicum powder 1.08%, celery seed powder 1.08%, aloe vera extract 1.08%, bilberry extract 2.69%, devil's claw powder 2.69%.

The ingredients, all available commercially in dry form, are blended together using a standard plow blender (American Process CPB-45) in a continuous mixing operation in which such ingredients are added in the following sequence: cat's claw powder, sarsaparilla root, licorice root, kelp, burdock root powder, alfalfa powder, barley grass, echinacea root, yucca extract, capsicum powder together with celery seed powder and aloe vera powder, and bilberry extract together with devil's claw powder. Activation of the choppers of the blender for approximately 2 minutes results in a substantially homogenous blend of herbal components.

EXAMPLE 2

The herbal blend of Example 1 may be blended with other ingredients as follows to produce the dietary supplement in the form of a dry powder:

| | |
|---|---|
| Herbal blend | 6.68% |
| Enzymatically hydrolyzed collagen ("Arthred", Traco Labs, Inc.) | 82.35% |
| Glucosamine sulfate | 3.18% |
| Turmeric | 0.46% |
| Boswellia serrata | 0.02% |
| Piper nigrum extract ("Bioperine") | 0.06% |
| Borage oil powder | 1.06% |
| Ashwagandha | 0.59% |
| Ginkgo biloba | 2.82% |
| Flavoring agent | 1.28% |
| Lecithin | 1.5% |

Using a conventional plow blender (American Process CPB-45) set for continuous mixing, the enzymatically hydrolyzed collagen in the form of a dry powder ("Arthred") is introduced into the mixing chamber with the blender in operation. Lecithin is then added gradually and the choppers are turned on for approximately 2 minutes, followed by the addition of the other dry ingredients in the following sequence: glucosamine sulfate, curcumin 95% (turmeric), *boswellia serrata*, "Bioperine" (*piper nigrum* extract), herbal blend (of Example 1), borage oil powder, natural pineapple flavoring, ashwagandha, and ginkgo biloba. The choppers are again turned on for a period of an additional 2 minutes to produce a uniformly-mixed dietary supplement embodying the invention.

The dietary supplement prepared in accordance with Examples 1 and 2 takes the form of a fine dark-yellow powder that is consumed enterally as a beverage. 7 g to 10 g of the essentially dry mixture, optimally 8.5 g of that mixture, is mixed with water, juice, milk, or any other suitable beverage. The recommended serving should be consumed once each day.

While in the foregoing we have disclosed an embodiment of the invention in considerable detail for purposes of illustration, it will be understood by those skilled in that art that many of these details may be varied without departing from the spirit and scope of the invention.

What is claimed is:

1. A dietary supplement for nutritionally promoting healthy joint function comprising an essentially dry mixture of the following ingredients in a daily serving of 7 g to 10 g: 78% to 90% protein derived from the enzymatic hydrolysis of collagen; 2% to 5% glucosamine sulfate; 2% to 3.5% ginkgo biloba (*Salsburia adiantifolia*); 0.8% to 1.2% borage oil powder (*Borago officinalis*)); 0.3% to 0.6% turmeric (*Curcuma longa*); 0.01% to 0.03% *Boswellia serrata*; 0.5% to 0.7% ashwagandha (*Withania sominfera*); 0.04% to 0.06% *Piper nigrum* extract; and 5% to 10% herbal blend.

2. The dietary supplement of claim 1 in which said herbal blend contains up to 20% of each of the following ingredients in said herbal blend: cat's claw powder (*Uncaria tomentosa*), sarsaparilla root (*Smilax ornata*), licorice root (*Glycyrrhiza glabra*), kelp (*Ascophyllum nodosum*), burdock root powder (*Arctium lappa*), alfalfa powder (*Medicajo sativa*), barley grass (*B. Hordeum vulgare L.*), and echinocea root (*Echinacea purpurea*).

3. The dietary supplement of claim 2 in which said herbal blend also contains 0% to 7% each of the following: yucca extract (*Yucca schidigera*), bilberry extract (*Vaccinium myrtillus*), devil's claw powder (*Harpagophytum procumens*), capsicum powder (*Capsicum annum linne*), celery seed powder (*Apium gaveolens*), and aloe vera powder (*Aloe barbadenis*).

4. The dietary supplement of claim 3 in which said ingredients of said herbal blend have the following weight percentages of said herbal blend: cat's claw powder 10.75%, sarsaparilla root 10.75%, licorice root 10.75%, kelp 10.75%, burdock root powder 10.75%, alfalfa powder 10.75%, barley grass 10.75%, echinocea root 10.75%, yucca extract 5.38%, bilberry extract 2.69%, devil's claw powder 2.69%, capsicum powder 1.08%, celery seed powder 1.08%, aloe vera powder 1.08%.

5. The dietary supplement of claim 1 in which said mixture has the following proportions of ingredients in weight percentage: 82.35% protein derived from the enyzmatic hydrolysis of collagen, 3.18% glucosamine sulfate, 2.82% ginkgo biloba, 1.06% borage oil powder, 0.46% turmeric, 0.02% *boswellia serrata*, 0.59% ashwagandha, 0.06% *piper nigrum* extract, 6.68% herbal blend, 1.5% lecithin, and 1.28% flavoring agents.

* * * * *